United States Patent [19]

Kiwala et al.

[11] 4,306,096
[45] Dec. 15, 1981

[54] CYCLOHEXYL PHENETHYLETHER

[75] Inventors: Jacob Kiwala, Brooklyn, N.Y.; Richard J. Tokarzewski, Keyport, N.J.; Frederick L. Schmitt, Holmdel, N.J.; Mark A. Sprecker, Sea Bright, N.J.

[73] Assignee: International Flavors & Fragrances Inc., New York, N.Y.

[21] Appl. No.: 192,238

[22] Filed: Sep. 30, 1980

[51] Int. Cl.$^3$ .............................................. C07C 43/168
[52] U.S. Cl. ................................. 568/659; 252/522 R; 424/84
[58] Field of Search ........................................ 568/659

[56] References Cited
PUBLICATIONS

Conrad et al., Chem. Abs., vol. 53 (1959) 18900g–18901b.

*Primary Examiner*—Bernard Helfin
*Attorney, Agent, or Firm*—Arthur L. Liberman

[57] ABSTRACT

Described is the compound cyclohexyl phenethylether having the structure:

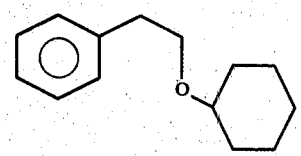

which has been found to be useful in augmenting or enhancing the aroma of perfumes and perfumed articles as well as colognes and, in addition, in combatting tobacco beetles of the species *Lasioderma serricorne* (F.)

1 Claim, 7 Drawing Figures

GLC PROFILE, EXAMPLE I DISTILLATION FRACTION 8.

GLC PROFILE, EXAMPLE I. REACTION PRODUCT PRIOR TO DISTILLATION.

PEAK "B"

PEAK "A"

GLC PROFILE FOR EXAMPLE I. DISTILLATION FRACTION 10.

GLC PROFILE FOR EXAMPLE I. DISTILLATION FRACTION 12.

NMR SPECTRUM FOR PEAK "A" OF EXAMPLE I.

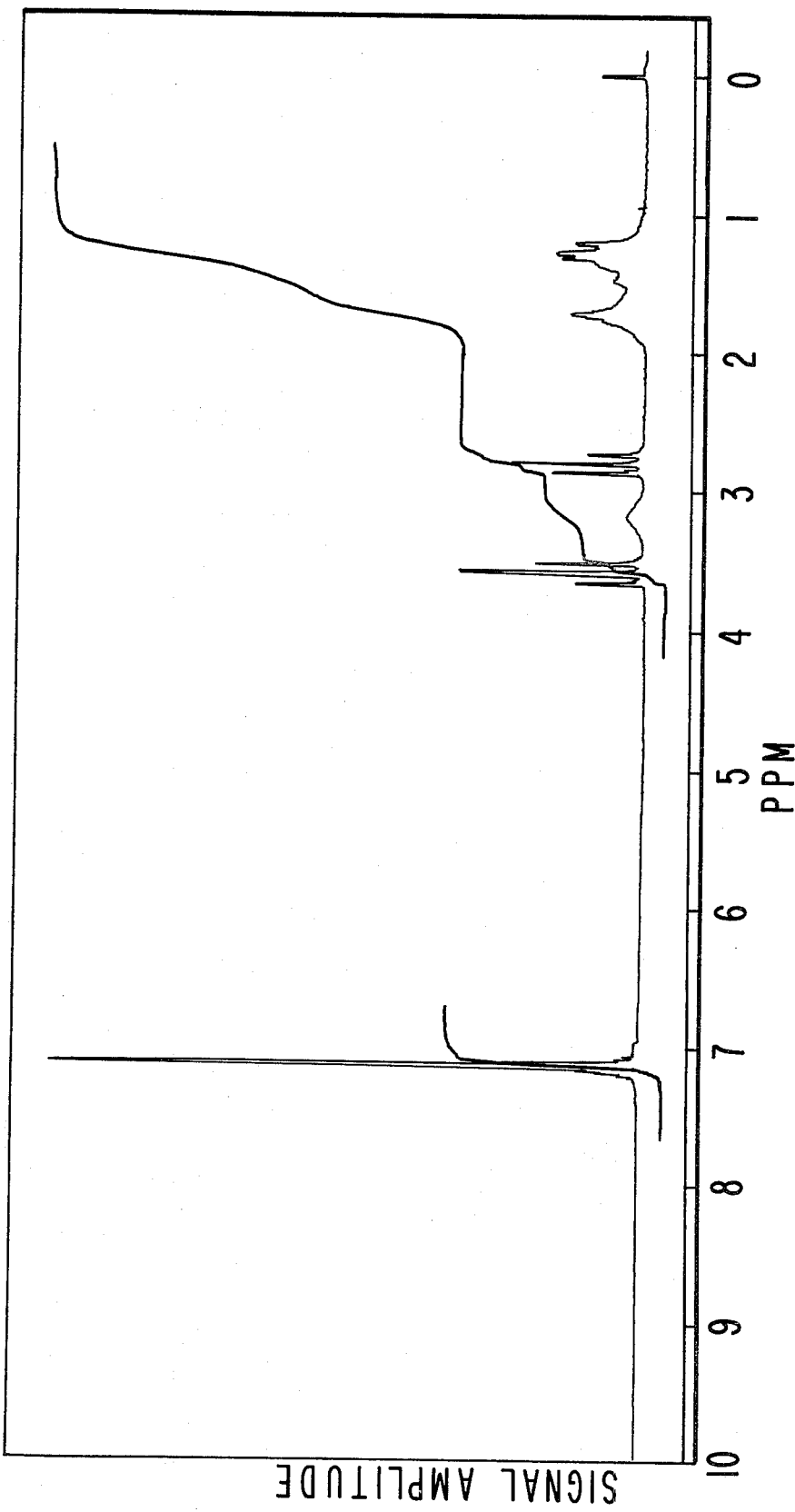

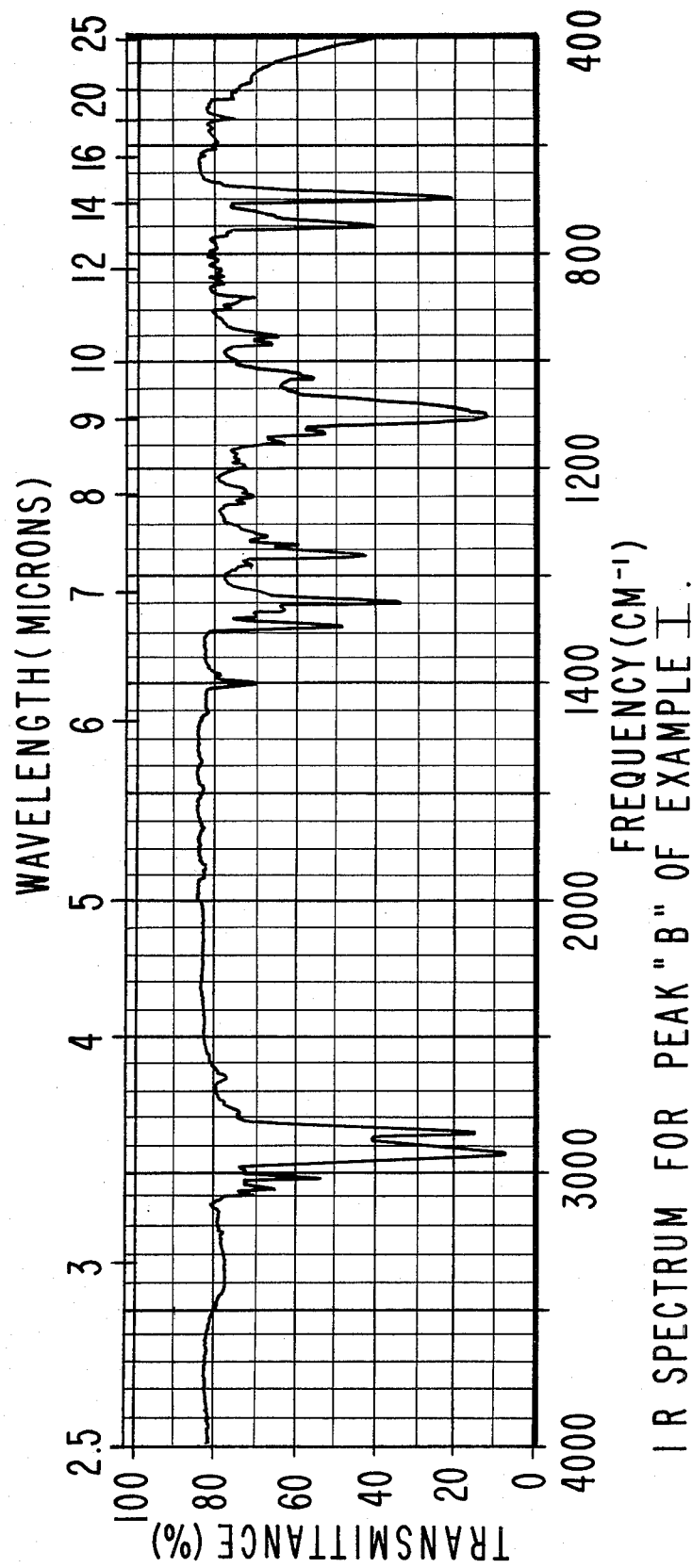

CYCLOHEXYL PHENETHYLETHER

BACKGROUND OF THE INVENTION

This invention relates to phenethyl cyclohexylether and to the use thereof in combatting insects as a result of the discovery that cyclohexyl phenethylether is a tobacco beetle pheromone or ectohormone; and in addition to the use of phenethyl cyclohexylether in augmenting or enhancing the aroma of perfumes, colognes and perfumed articles (e.g. solid or liquid, anionic, cationic, nonionic or zwitterionic detergents, fabric softeners, fabric softener articles, hair conditioners, odorants and deodorants). Obviously then, the invention also relates to a pleasant smelling pheromone or ectohormone useful for combatting insects yet, at the same time, not repulsive to the individual or group of individuals applying the pheromone or ectohormone to the area where the insects are to be combatted.

Pheromones or ectohormones are secreted by insects as so called socially active ingredients e.g., as sexual attractant or aggregation substance. The use of these pheromones or ectohormones is known to attract insects into certain small sections of a contaminated area, to concentrate them in this area and then to destroy the insects in any known way, e.g., mechanically, chemically or with insecticides. This method leads to a very economical and concentrated use of the actual insecticides, especially of insecticides which are ecologically dangerous, whereby the spraying of large parts of the contaminated area in an expensive way e.g., by spraying insecticides with an aeroplane, is avoided.

No pheromones have been discovered up to the present time for use with *Lasioderma serricorne* (F.). Thus, the pheromones known up to the present time belong to a large variety of chemical substances and are, as a rule, effective only with respect to certain insects such as, for example, for use in combatting insects of the order coleoptera and the family scolytidae and platypodidae which beetles cause substantial damage to forests and to the wood of trees generally as taught in U.S. Pat. No. 3,927,207 issued on Dec. 16, 1975.

Another problem as yet unsolved by the prior art concerns the utilization, either in conjunction with or as pheromones or ectohormones for insect attractants, of fragrance imparting, augmenting or enhancing agents. Such fragrance imparting, augmenting or enhancing agents must be either identical to or, at the very least, compatible with the pheromones or ectohormones. Previously such pheromones or ectohormones having their own aroma profiles usually have an aroma profile which either was esthetically displeasing or, at the very best, incapable of covering or deodorizing the chemical-like sharp, abrasive aroma of the insecticides used against the insects.

An optimal solution to the foregoing problems would be to create, in one chemical, a pheromone or ectohormone; an insecticide; and an aroma augmenting or enhancing substance which is compatible with said pheromone or ectohormone and with said insecticide.

Notwithstanding the aforementioned pheromone or ectohormone properties and notwithstanding the aforementioned insecticide properties, chemical compounds which can provide dry green hyacinth-like, rose-like and galbanum-like aromas which are both rich and full bodied as well as long lasting and desirable in the art of perfumery. Many of the natural materials which provide such fragrances and contribute such desired nuances to perfumery compositions are high in cost, unattainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of these synthetic materials either have the desired nuances only to a relatively small degree or else contribute undesirable or unwanted odor to the compositions. The search for materials which can provide more refined, more natural-like long lasting dry green hyacinth, rose and galbanum aromas have been difficult and relatively costly in the areas of both natural products and synthetic products.

Arctander in "Perfume and Flavor Chemicals (Aroma Chemicals)", Volume II, 1969 described phenylethyl alcohol as having a rose aroma.

Phenethyl propionate has been disclosed in the Journal of Economic Entomology 66 (5), 1973, and has been indicated by McGovern et al. to be an attractant for *Popillia japonica Newman* (Japanese beetles) particularly in combination with eugenol. Indeed in that same paper by McGovern et al., it is indicated that trans-2-hexenal, a well known perfume ingredient, is also a Japanese beetle attractant. The phenethyl propionate has the structure:

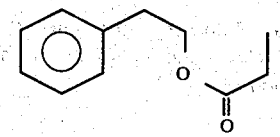

In another paper by McGovern et al., Journal of Economic Entomology, Volume 63, Number 1, page 276, it is indicated that methyl cyclohexanepropionate and certain related chemicals are also attractants for *Popillia japonica Newman*.

Research concerning *Lasioderma serricorne* (F.) and attractants therefor are limited to the use of extracts of natural food odors. Thus, the paper by Fletcher and Garrett entitled "Ovipositional Response of Three Strains of the Cigarette Beetle to Extracts of Food Odors" in Tobacco International, 182 (5), pages 166–169, Mar. 7, 1980. Fletcher and Garrett disclose that the ovipositional response of three strains of the cigarette beetle is a function of different food odor attractants.

Nothing in the prior art, however, discloses the unexpected, unobvious and advantageous properties of phenethyl cyclohexylether which is not only useful per se for augmenting or enhancing the aroma of perfume compositions, colognes and perfumed articles but is also useful as an *Lasioderma serricorne* (F.) pheromone and, in addition, as an *Lasioderma serricorne* (F.) insecticide.

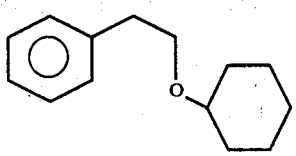

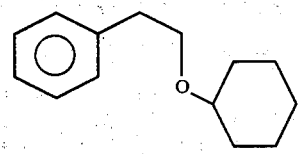

Figure 1B:
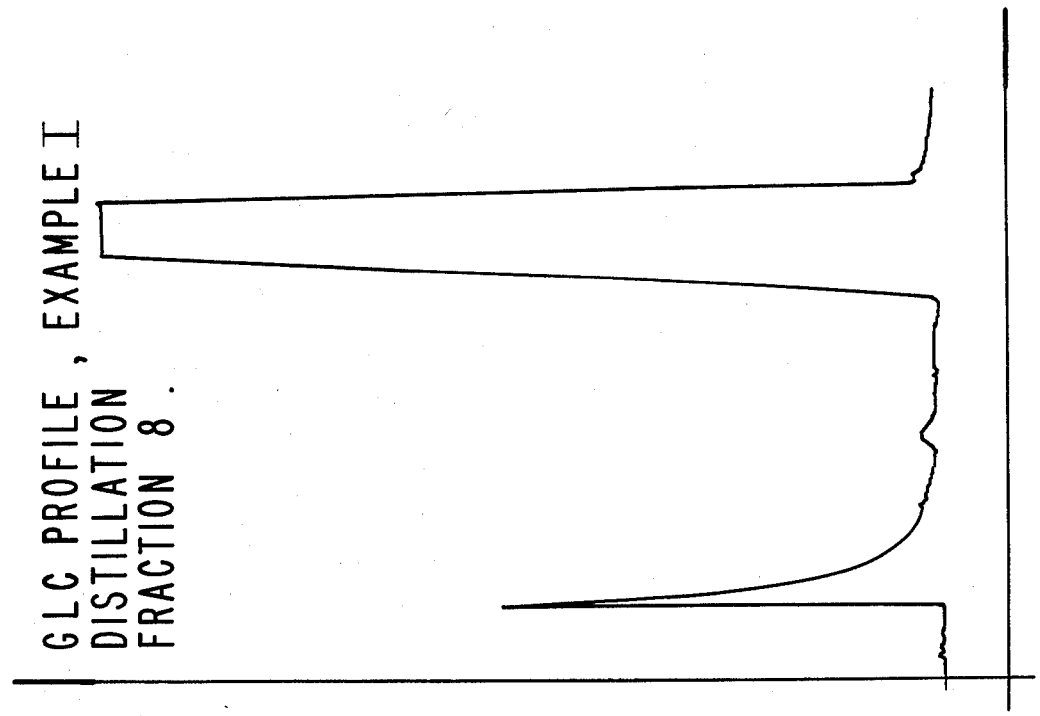
FIG. 1B is the GLC profile for fraction 8 of the distillation product of the reaction product of Example I which contains phenethyl cyclohexylether having the structure.
Figure 1A:
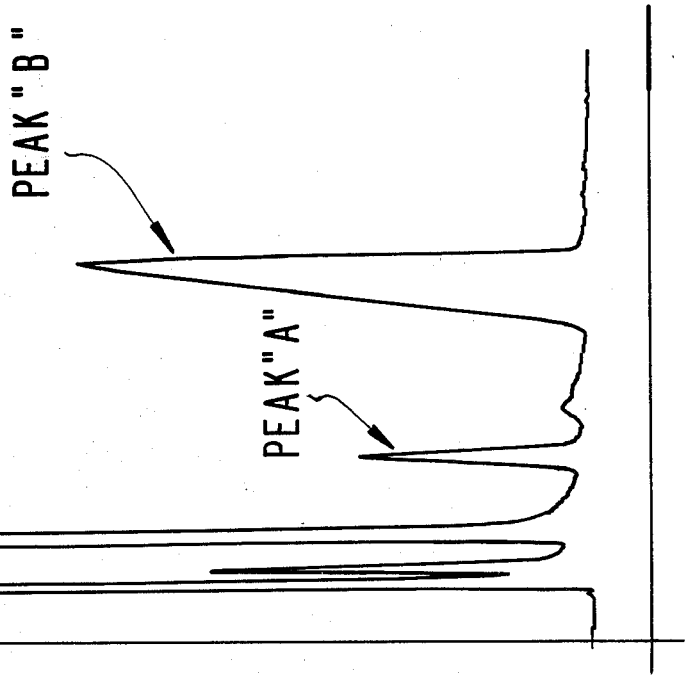
FIG. 1A is a GLC profile for the reaction product at the end of the reaction and just prior to distillation.
Figure 1C:
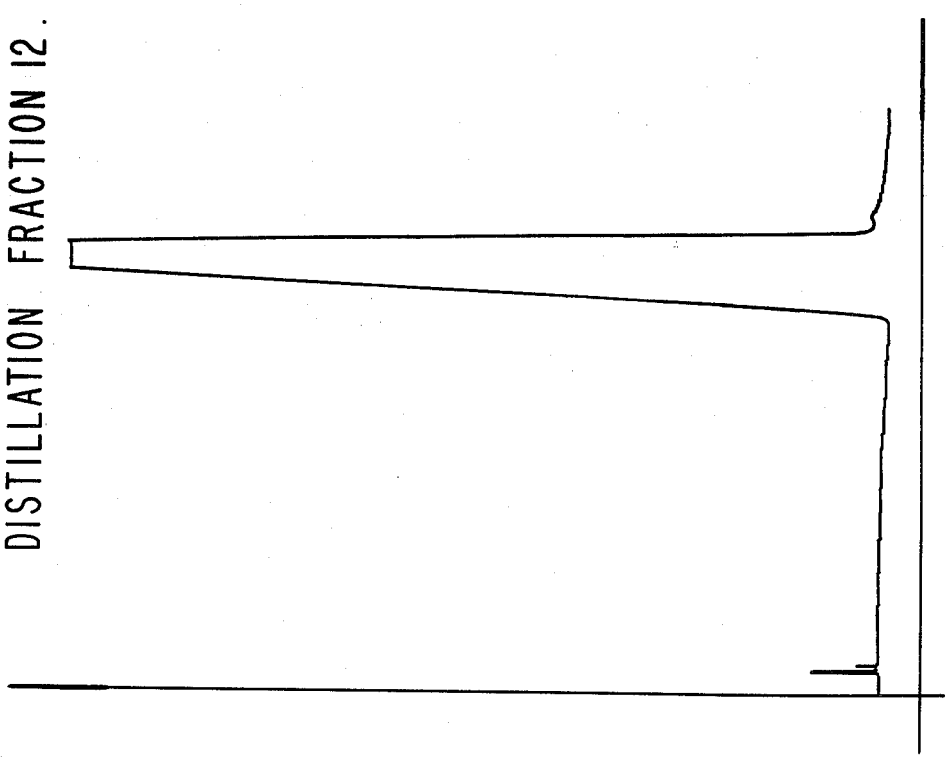

FIG. 1C is the GLC profile for fraction 10 of the distillation product of the reaction product of Example I containing the compound having the structure:

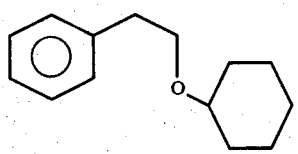

Figure 1D:
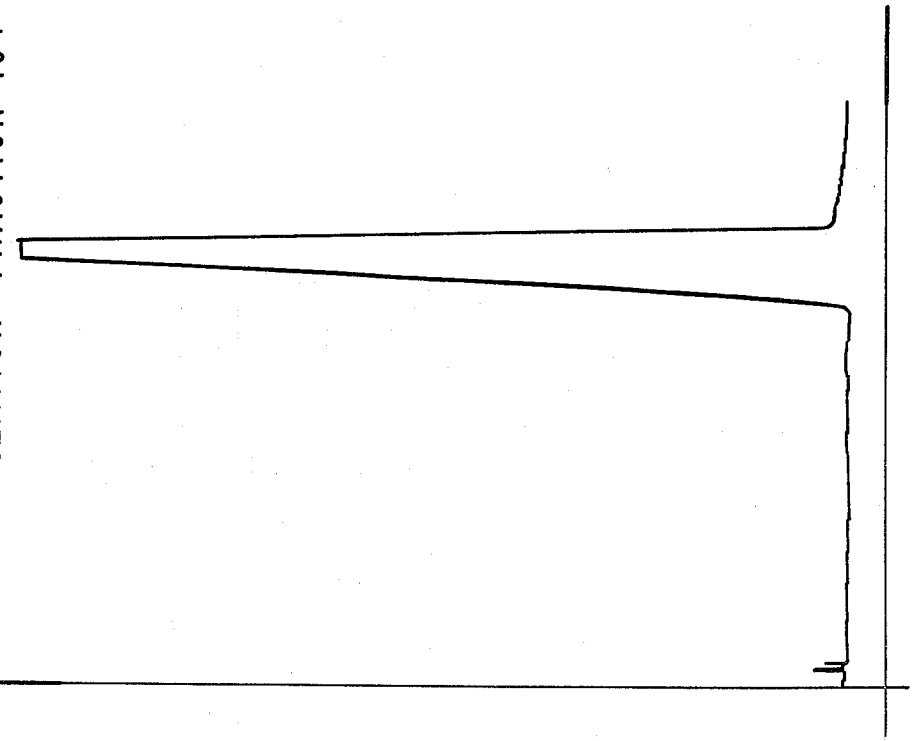

FIG. 1D is the GLC profile for fraction 12 of the distillation product of the reaction product of Example I containing the compound having the structure:

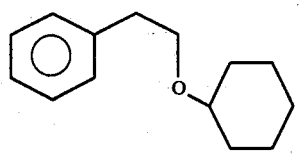

Figure 2:
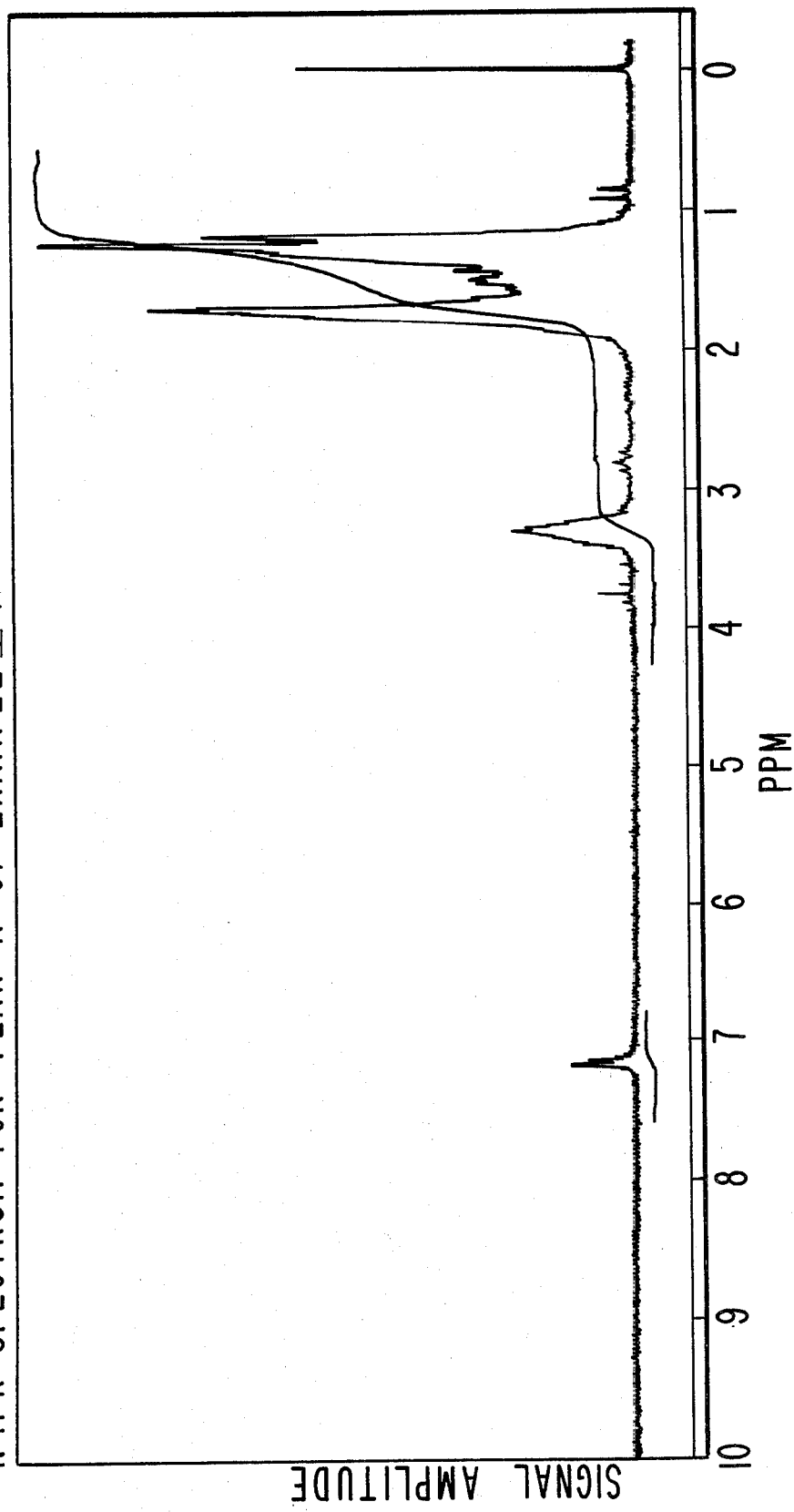

FIG. 2 is a NMR spectrum for peak "A" of the GLC profile of FIG. 1A which consists of the compound having the structure:

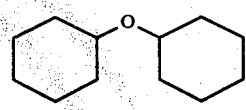

FIG. 3 is the NMR spectrum for peak "B" of the GLC profile of FIG. 1A containing the compound having the structure:

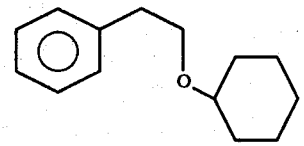

FIG. 4 is the infra-red spectrum for peak "B" of the GLC profile of FIG. 1A containing the compound having the structure:

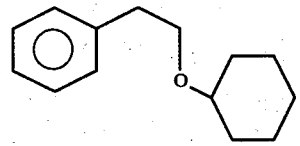

THE INVENTION

The present invention proposes the use of cyclohexyl phenethylether having the structure:

for combatting beetles of the order *Lasioderma serricorne* (F.) in such a manner that the cyclohexyl phenethylether not only acts as a pheromone or ectohormone but also acts as an aroma augmenting or enhancing agent and, in addition, acts as an insecticide. Notwithstanding the pheromone and insecticide properties of cyclohexyl phenethylether, the instant invention also provides cyclohexyl phenethylether as a fragrance capable of augmenting or enhancing the fragrance of perfume compositions, colognes and perfumed articles (e.g., solid or liquid, anionic, cationic, nonionic or zwitterionic detergents, fabric softeners, dryer-added fabric softener articles, hair conditioners, deodorants, and cosmetic powders).

The cyclohexyl phenethylether of our invention is capable of augmenting or enhancing the dry green hyacinth, rose and galbanum aromas of perfumes, perfumed articles and colognes of our invention. Of course, as part of the perfumed articles of our invention is the "perfumed insecticide-pheromone" compositions of our invention.

The destruction of the *Lasioderma serricorne* (F.) insects can be achieved by distributing the cyclohexyl phenethylether or pheromonal attractants in the contaminated area at separate individual places, namely, by means of catch trees. These are impregnated with the attractants which may, if desired, act as an insecticide too; or the cyclohexyl phenethylether may be augmented by additional insecticide whereupon the catch trees are sprayed with another insecticide either before or after the insects have gathered at the catch tree (whatever insects are still alive after contact with the cyclohexyl phenethylether). Instead of using the cyclohexyl phenethylether alone or taken together with another insecticide, one may also use a chemical sterilizing compound. Further, the catch tree may be treated with other chemicals or can be burned. Another possible method for destroying insects with the cyclohexyl phenethylether according to our invention makes use of the disturbance or perturbance theory. Instead of physically destroying the insects with either high concentrations of the cyclohexyl phenethylether or by using the chclohexyl phenethylether followed by additional insecticide, it is also possible to combine the cyclohexyl phenethylether physically with additional stronger insecticide before using. Thus, it is possible now to spray a combination of cyclohexyl phenethylether which has a pleasant aroma in combination with insecticide whose original aroma is covered using the cyclohexyl phenethylether in certain centrally located area or in the form of rows in the contaminated area. Furthermore, cyclohexyl phenethylether can be mixed with the usual solid or liquid carriers or with biocides such as stronger insecticides, pesticides or herbicides. The mixture may contain surface active agents to obtain a better distribution or adherence to the plants.

The cyclohexyl phenethylether of our invention may be prepared by reacting cyclohexanol with beta phenylethyl alcohol in the presence of an acid such as sulfuric acid according to the reaction:

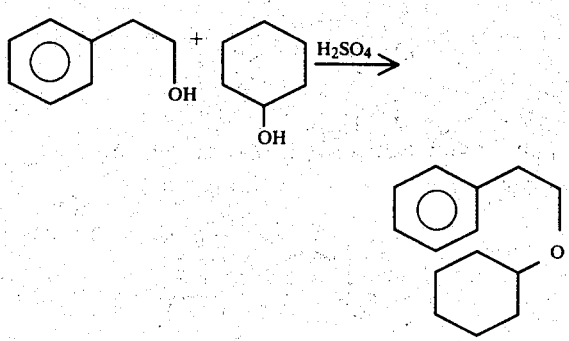

Alternatively, sodium phenylethyl alcoholate may be reacted with cyclohexyl chloride or sodium cyclohexyl alcoholate may be reacted with beta phenylethyl chloride or beta phenylethyl bromide by means of a "Williamson" synthesis, conventional in the organic chemistry art.

Notwithstanding the pheromonal and insecticidal activity of the cyclohexyl phenethylether of our invention, the cyclohexyl phenethylether of our invention can be used to contribute long lasting dry green hyacinth, rose and galbanum aromas which are unexpectedly full and rich for a very long period of time to perfumes, perfumed articles and colognes. As olfactory agents, the cyclohexyl phenethylether of our invention can be formulated into or used as components of a "perfume composition" or can be used as components of a "perfumed article" or the perfume composition may be added to "perfumed articles".

The term "perfume composition" is used herein to mean a mixture of organic compounds including, for example, alcohols, aldehydes, ketones, nitriles, ethers in addition to and other than the cyclohexyl phenethylether of our invention, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatures which include odorous substances which lend a particular note to the perfume throughout all stages of evaporation, and substances which retard evaporation; and (d) top notes which are usually low-boiling, fresh-smelling materials.

In perfume compositions, the individual component will contribute its particular olfactory characteristics, but the overall effect of the perfume composition will be the sum of the effects of each of the ingredients. Thus, the cyclohexyl phenethylether of our invention can be used to alter the aroma characteristics of a perfume composition, for example, by highlighting or moderating the olfactory reaction contributed by another ingredient in the composition.

The amount of cyclohexyl phenethylether of our invention which will be effective in perfume compositions depends upon many factors, including the other ingredients, their amounts and the effects which are desired. It has been found that perfume compositions containing as little as 0.05% of the cyclohexyl phenethylether of our invention or even less can be used to impart long lasting interesting very strong dry green hyacinth, rose and galbanum aromas to soaps, liquid and solid, cationic, nonionic, anionic and zwitterionic detergents, cosmetic powders, liquid and solid fabric softeners, dryer-added fabric softener articles, optical brightener compositions and other products. The amount employed can range up to 50% or more and will depend upon considerations of cost, nature of the end product and the effect desired on the finished product and particular fragrance sought.

The cyclohexyl phenethylether of our invention can be used alone or in a perfume composition as an olfactory component in detergents and soaps, space odorants and deodorants; perfumes; colognes, toilet waters; bath salts; hair preparations such as lacquers, brilliantines, pomades and shampoos; cosmetic preparations such as creams, deodorants, hand lotions and sun screens; powders such as talcs, dusting powders, face powder and the like. When used as an olfactory component of a perfumed article, as little as 0.01% of the cyclohexyl phenethylether will suffice to impart an interesting long lasting dry green hyacinth, rose and galbanum aroma. Generally, no more than 0.5% is required in the perfumed article.

In addition, the perfume composition can contain a vehicle or carrier for the cyclohexyl phenethylether alone or with other ingredients. The vehicle can be a liquid such as an alcohol such an ethanol, a glycol such as propylene glycol, or the like. The carrier can be an absorbent solid such a gum or components for encapsulating the composition such as gelatin which can be used to form a capsule wall surrounding the perfume oil by means of coacervation.

It will thus be apparant that the cyclohexyl phenethylether of our invention can be utilized to alter, modify, augment or enhance the aroma of a wide variety of consumable materials including fragrance formulations, colognes, pheromones and perfumed articles in general.

The following examples serve to illustrate our invention and this invention is to be considered restricted thereto only as indicated in the appended claims.

All parts and percentages given herein are by weight unless otherwise specified.

EXAMPLE I

PREPARATION OF CYCLOHEXYL PHENETHYLETHER

Reaction:

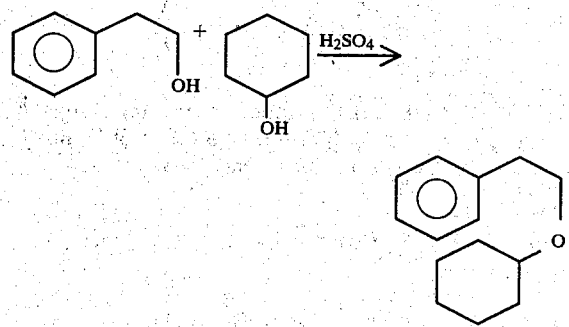

Into a 2 liter reaction vessel equipped with stirrer, thermometer, heating mantle and overhead condenser with azeotrope takeoff apparatus is placed 488 grams of betaphenylethyl alcohol; 440 grams of cyclohexanol and 100 grams of concentrated sulfuric acid. The reaction mass is then heated to a temperature of 115° C. and maintained at a temperature in the range of 104°–127° C. at reflux while azeotropically removing 80 ml water, for a period of 3 hours. At the end of the 3 hour period, a sample is analyzed by means of GLC analysis (conditions: 180° C. isothermal using an SE-30 packed column). FIG. 1A is the GLC profile of the reaction product at this point.

The resulting reaction mass is then distilled on a 1'×29/42 distillation column yielding the following fractions:

| Fraction Number | Vapor Temp. °C. | Liquid Temp. °C. | Vacuum mm. Hg pressure | Reflux Ratio R/D |
| --- | --- | --- | --- | --- |
| 1 | 27 | 40 | 1.2 | 1 |
| 2 | 70 | 100 | 1.0 | 4/1 |
| 3 | 67 | 100 | 1.0 | 4/1 |
| 4 | 67 | 100 |  | 4/1 |
| 5 | 70 | 105 | 0.7 | 4/1 |
| 6 |  |  |  | 4/1 |
| 7 | 70 | 130 | 0.7 | 4/1 |
| 8 | 88 | 140 |  | 4/1 |
| 9 | 100 | 132 | 0.55 | 4/1 |
| 10 | 100 | 160 |  | 4/1 |
| 11 | 100 | 165 |  | 4/1 |
| 12 | 102 | 185 | 0.4 | 4/1 |
| 13 | 107 | 205 | 0.5 | 4/1 |

FIG. 1B is the GLC profile for fraction 8 of the distillation product of the reaction product of Example I which contains phenethyl cyclohexylether having the structure:

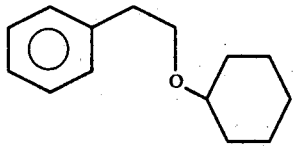

FIG. 1C is the GLC profile for fraction 10 of the distillation product of the reaction product of Example I containing the compound having the structure:

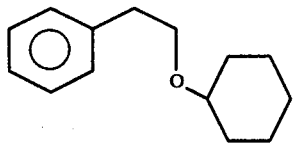

FIG. 1D is the GLC profile for fraction 12 of the distillation product of the reaction product of Example 1 containing the compound having the structure:

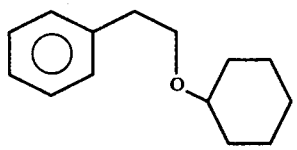

FIG. 2 is the NMR spectrum for peak "A" of the GLC profile of FIG. 1A which consists of the compound having the structure:

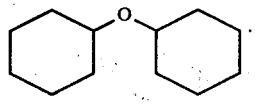

FIG. 3 is a NMR spectrum for peak "B" of the GLC profile of FIG. 1A containing the compound having the structure:

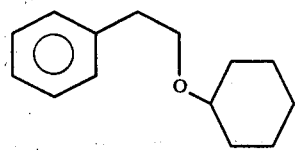

FIG. 4 is the infra-red spectrum for peak "B" of the GLC profile of FIG. 1A containing the compound having the structure:

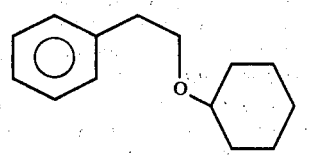

EXAMPLE II

Field tests are made each time using 100 male and 100 female *Lasioderma serricorne* (F.) cigarette beeetles. The beetles were released at a certain distance from the source of attraction which was treated with cyclohexyl phenethylether prepared according to Example I. Further, felled trees having already been contaminated with the respective beetles are positioned at both sides of the starting point. After a certain period of time the amount of insects gathered at the source of attraction was determined thus indicating the effectiveness of the pheromonal mixture according to the invention.

Field tests with *Lasioderma serricorne* (F.) are made whereby the distance between the starting point and the source of attraction is 50 meters. Four independent field tests were made whereby 42% of the male beetles and 46% of the female beetles gathered at each catch tree. The concentration of insects at the catch tree was 55% of the male insects and 58% of the female insects. In all these tests the catch tree was impregnated with a 0.7% ethanolic solution of cyclohexyl phenethylether (7 gm. cyclohexyl phenethylether per 92 gm. of 95% aqueous ethanol).

EXAMPLE III

During two consecutive days several felled oak trees surrounding a field of tobacco plants were treated with 250 mg of phenethyl cyclohexylether in 1.0% ethanolic solution. These trees were exposed in an area which were contaminated with *Lasioderma serricorne* (F.). After 3 to 4 days 100 bettles per square meter were observed on the logs. Other untreated logs or trees in the direct neighborhood of the treated logs or trees showed very few (about 12) insects per square meter on the average while other trees at a distance of 10 to 20 meters showed no contamination.

EXAMPLE IV

In a large test field, mixtures of cyclohexyl phenethylether in admixture with different DDT preparations, fluorine-containing mixtures and arsen-containing mixtures as well as hexachloro-cyclohexane were used. These mixtures contained also small amounts of surface-active agents and carriers. The mixtures were applied to catch trees namely logs of oak trees in an area of tobacco plants contaminated with *Lasioderma serricorne* (F.) The distance between the catch trees was always 200 meters. After 8 days there was no contamination either in the tobacco fields or around the oak trees. About 92% of the *Lasioderma serricorne* (F.) insects were destroyed. Surprisingly, it was found that after the fourth day the attracting effect was not diminished in spite of dead insects being present. Furthermore, in those areas where cyclohexyl phenethylether was used alone, the average number of insects destroyed was about 80% which in itself is surprising. Thus, the cyclohexyl phenethylether not only acts as a pheromone but also as an insecticide. Furthermore, the entire area wherein the cyclohexyl phenethylether was used had a faint pleasant floral aroma covering any adverse and esthetically displeasing aroma of any other insecticides that were used.

EXAMPLE V

The following mixture is prepared:

| Ingredients | Parts by Weight |
|---|---|
| Phenylacetic acid | 70.0 |
| Coumarin | 20.0 |
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| Cyclohexyl phenethylether | 30.0 |

The cyclohexyl phenethylether prepared according to Example I imparts the dry green hyacinth, rose, galbanum-like aroma to this honey fragrance while giving it a very warm undertone and imparting a very long lasting floral top note to this fragrance.

EXAMPLE VI

PREPARATION OF A COSMETIC POWDER COMPOSITION

A cosmetic powder is prepared by mixing in a ball mill 100 grams of talcum powder with 0.25 grams of the perfume composition prepared according to Example V. It has an excellent floral aroma.

EXAMPLE VII

PERFUMED LIQUID DETERGENT

Concentrated liquid detergents (Lysine salt of n-dodecylbenzene sulfonic acid as more specifically described in U.S. Pat. No. 3,948,818 issued on Apr. 6, 1976) with floral aroma nuances and rose, galbanum and hyacinth-like top notes are prepared containing 0.10%, 0.15% and 0.20% of the fragrance prepared according to Example V. They are prepared by adding and homogeneously mixing the appropriate quantity of fragrance formulation prepared according to Example V in the liquid detergent. The detergents all possess excellent floral aromas with dry green hyacinth, rose and galbanum nuances, the intensity increasing with greater concentrations of perfume composition prepared according to Example V.

EXAMPLE VIII

PREPARATION OF A COLOGNE AND HANDKERCHIEF PERFUME

The composition prepared according to Example V is incorporated into a cologne at concentrations of 2.0%, 2.5%, 3.0%, 4.0%, 4.5% and 5.0% in 80%, 85%, 90% and 95% aqueous food grade ethanol; and into handkerchief perfumes at concentrations of 15%, 20% and 30% (in 80%, 85% and 95% aqueous food grade ethanol). A distinctive and definitive dry green hyacinth, rose, galbanum, rich and full-bodied floral aroma is imparted to the cologne and to the handkerchief perfume at all levels indicated.

EXAMPLE IX

PREPARATION OF SOAP COMPOSITION 100 grams of soap chips are mixed with 1 gram of the formulation of Example V until a homogeneous composition is obtained. The homogeneous composition is heated under three atmospheres pressure at 180° C. for a period of three hours and the resulting liquid is placed into soap molds. The resulting soap cakes, on cooling, manifest excellent floral aromas with dry green hyacinth, rose and galbanum nuances that are very long lasting.

EXAMPLE X

PREPARATION OF A SOLID DETERGENT COMPOSITION

A detergent is prepared from the following ingredients according to Example I of Canadian Pat. No. 1,007,948:

| | Percent by Weight |
|---|---|
| "Neodol 45-11" (a $C_{14}$–$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate free" detergent. A total of 100 grams of this detergent is admixed with 0.15 grams of the honey based perfume of Example V. Each of the detergent samples have an excellent floral honey-like, dry green hyacinth, rose and galbanum aroma.

EXAMPLE XI

DRYER-ADDED FABRIC SOFTENER ARTICLE

Utilizing the procedure of Example I at colume 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):

57% $C_{20-22}$ HAPS

22% isopropyl alcohol
20% antistatic agent
1% of cyclohexyl phenethylether produced according to Example I A fabric softening composition prepared as set forth above having a dry green hyacinth, rose, galbanum and generally floral aroma characteristic consists of a substrate having a weight of about 3grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. A pleasant floral aroma is imparted in a pleasant manner to the head space in the dryer on operation thereof using the said dryer-added fabric softening nonwoven fabric.

EXAMPLE XII

A liquid detergent composition prepared according to Example IV of United Kingdom Pat. No. 1,498,520 whereby the following ingredients are admixed:

| Ingredient | Weight % |
| --- | --- |
| Coconut alcohol ethoxylate | 30% |
| Linear alkyl benzene sulfonate, triethanolamine salt (alkyl = $C_{11.8}$ avg.) | 10% |
| Potassium chloride | 3% |
| Triethanolamine | 3% |
| Triethanolammonium citrate | 2% |
| Ethyl alcohol | 5% |
| Soil release ether "D" | 1.0% |
| Cyclohexyl phenethylether prepared according to Example I | 3.0% |
| Water | Balance |

The soil release ether "D" is defined according to Table II on page 15 of United Kingdom Pat. No. 1,498,520.

This composition is prepared by admixing all of the ingredients exclusive of soil release ether "D" and agitating the mixture until all electrolytes are dissolved. Soil release ether "D" is then admixed with the solution in the form of a dry powder which passes through a 150 mesh standard sieve. The resulting composition is in the liquid state and is easily pourable. The composition is found not to redden on contact with plastic bottles, does not gel when diluted with water and has a long-lasting aroma which can be described as dry green hyacinth, rose, galbanum and rich and rather long lasting. Indeed, the aroma lasts for several weeks when exposed to the atmosphere.

This composition is added to an aqueous laundrying bath at a concentration of 0.20% (weight) at a temperature of 55° C., water hardness 7 grains per gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics has a pleasant faint aroma which can be described as hyacinth, rose, and galbanum and also rather long-lasting (about 3 days).

EXAMPLE XIII

PREPARATION OF A COSMETIC POWDER COMPOSITION

A cosmetic powder is prepared by admixing in a ball mill 100 grams of talcum powder with 0.25 grams of phenethyl cyclohexylether prepared according to Example I. The resulting cosmetic powder has an excellent dry green hyacinth, rose, galbanum, rich and full-bodied floral fragrance which is very long-lasting.

EXAMPLE XIV

PERFUMED LIQUID DETERGENT

Concentrated liquid detergents (Lysine salt of n-dodecylbenzene sulfonic acid as more specifically described in U.S. Pat. No. 3,948,818 isssued on Apr. 6, 1976) with dry green hyacinth, rose, galbanum rich and full-bodied floral aroma are prepared containing 0.10%, 0.15%, 0.20%, and 0.25% of cyclohexyl phenethylether prepared according to Example I. They are prepared by adding and homogeneously admixing the appropriate quantity of phenethyl cyclohexylether in the liquid detergent. The detergents all possess intense long-lasting dry green hyacinth, rose, galbanum and generally floral aroma characteristics.

EXAMPLE XV

PREPARATION OF COLOGNES AND HANDKERCHIEF PERFUMES

Cyclohexyl phenethylether prepared according to Example I is incorporated into colognes at concentrations of 2.0%, 2.5%, 3.0%, 3.5%, 4.0%, and 4.5% in 80%, 85%, 90% and 95% aqueous food grade ethanol; and into handkerchief perfumes at concentrations of 15%, 20%, 25% and 30% (in 80%, 90% and 95% aqueous ethanol). Distinctive dry green hyacinth, rose, galbanum, rich and full-bodied floral aroma nuances which are very long lasting on dry out (54 hours) are imparted to the colognes and to the handkerchief perfumes at the various above levels indicated.

What is claimed is:

1. Cyclohexyl phenethylether having the structure:

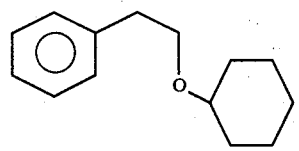

* * * * *